United States Patent [19]
Schroeder

[11] Patent Number: 5,152,184
[45] Date of Patent: Oct. 6, 1992

[54] THERMAL TEST LINER APPARATUS AND METHOD

[75] Inventor: Royce E. Schroeder, Spring, Tex.

[73] Assignee: OFI Testing Equipment, Inc., Houston, Tex.

[21] Appl. No.: 619,251

[22] Filed: Nov. 28, 1990

[51] Int. Cl.$^5$ ............................................. G01N 25/00
[52] U.S. Cl. ........................... 73/863.11; 73/864.91; 73/61.46; 220/284; 220/410; 374/45; 422/102
[58] Field of Search ........... 73/864.91, 863.11, 863.12, 73/866, 855.6, 864.62, 19.05, 19.06, 53, 54, 61.3, 61.4, 64.2; 324/45, 57; 422/102, 78, 80; 436/147, 148, 155; 435/285, 296, 310; 219/389; 215/16, 10, 363, 302, 296; 220/410, 345, 358, 284, 378, DIG. 12

[56] References Cited

U.S. PATENT DOCUMENTS

| | | | |
|---|---|---|---|
| H,962 | 9/1991 | Kovach | 73/863.1 X |
| 1,061,131 | 5/1913 | Seamans | 215/363 X |
| 2,260,419 | 10/1941 | Wrightsman | 73/864.62 |
| 2,662,393 | 12/1953 | Rzasa | 73/61.3 X |
| 3,401,565 | 9/1968 | Stoll et al. | 73/863.11 |
| 3,430,804 | 3/1969 | Bernas | 220/410 |
| 3,892,130 | 7/1975 | Winget et al. | 73/864.62 |
| 3,984,688 | 10/1976 | Von Bargen et al. | 422/52 X |
| 4,167,214 | 9/1979 | Street, Jr. | 166/307 |
| 4,554,436 | 11/1985 | Chlosta et al. | 219/389 X |
| 4,677,843 | 7/1987 | Schroeder | 422/209 X |

FOREIGN PATENT DOCUMENTS

| | | | |
|---|---|---|---|
| 61614 | 4/1984 | Japan | 73/864.62 |
| 186833 | 8/1986 | Japan | 73/866 |
| 1430794 | 10/1988 | U.S.S.R. | 73/864.62 |

*Primary Examiner*—Tom Noland
*Attorney, Agent, or Firm*—Neal J. Mosely

[57] ABSTRACT

A cast virgin TEFLON liner is provided for steel test cylinders used in thermal testing of a sample of drilling mud or additives. The liner has a hollow cylindrical body closed at one end and open at the other. A disc-shaped lid fits inside the open end of the liner and an elastomeric o-ring makes a tight seal between the liner and lid. A threaded hole in the center of the lid is closed with threaded plug. The apparatus includes a threaded metal tool or puller with T-shaped handle, for removing the liner from the test cylinder, and also for removing the lid from the liner. An internal air passageway in the puller from a first opening in the tip end of the puller to a second opening on one side of the shaft allows the lid to be removed from the liner without creating a vaccum in the space between the sample and the lid. For removing the liner from the test cylinder, the threaded shaft is screwed into the lid such that the second opening is covered and thereby creates a vacuum between the sample and lid when the liner is pulled out of the test cylinder. The liner and lid are made of cast virgin TEFLON to avoid dangerous chemical reactions, e.g., oxidative reactions, with carbon particles in molded or reused TEFLON.

16 Claims, 1 Drawing Sheet

THERMAL TEST LINER APPARATUS AND METHOD

BACKGROUND OF THE INVENTION

1. Field of the Invention

This invention relates generally to thermal testing, and more particularly to a cast virgin Teflon, viz., polytetrafluoroethylene or PTFE, liner to be placed in a test cylinder in an apparatus for thermal testing of oil well drilling mud and additives samples.

The present invention may be used in a testing apparatus such as that disclosed in Schroeder U.S. Pat. No. 4,677,843.

2. Brief Description of the Prior Art

Pertinent references in the prior art include Noteboom U.S. Pat. No. 3,941,661; Lynn U.S. Pat. No. B1 4,238,568; Keilman U.S. Pat. No. 4,717,668; and Mussi U.S. Pat. No. 4,912,058.

Noteboom U.S. Pat. No. 3,941,661 discloses a plastic spiral insert for use in roller culture bottles for cell culture. Lynn U.S. Pat No. B1 4,238,568 discloses a roller bottle having a plurality of sections which may be bonded after their interior surfaces have been treated to enhance cell adhesion. Keilman U.S. Pat. No. 4,717,668 discloses a plastic roller bottle for suspension cultures for bacteriology or other cell growth or maintenance. Mussi U.S. Pat. No. 4,912,058 discloses a roller bottle with provision for increased internal surface area for cell growth by the use of a foamed, textured or woven liner or sleeve into the bottle prior to use.

Each of these prior art references has the obvious limitation, compared to the present invention, of applying only to cell culture growth; they are not comparable to devices for testing samples at elevated temperature conditions.

The present invention is distinguished over the prior art in general, and these patents in particular, by a cast virgin Teflon liner for steel test cylinders used in thermal testing of a sample of drilling mud or additives. The liner has a hollow cylindrical body closed at one end and open at the other. A disc-shaped lid fits inside the open end of the liner and an elastomeric o-ring makes a tight seal between the liner and lid. A threaded hole in the center of the lid is closed with threaded plug. The apparatus includes a threaded metal tool or puller with T-shaped handle, for removing the liner from the test cylinder, and also for removing the lid from the liner. An internal air passageway in the puller from a first opening in the tip end of the puller to a second opening on one side of the shaft allows the lid to be removed from the liner without creating a vacuum in the space between the sample and the lid. For removing the liner from the test cylinder, the threaded shaft is screwed into the lid such that the second opening is covered and thereby creates a vacuum between the sample and lid when the liner is pulled out of the test cylinder. The liner and lid are made of cast virgin Teflon to avoid dangerous chemical reactions, e.g., oxidative reactions, with carbon particles in molded or reused Teflon.

SUMMARY OF THE INVENTION

It is therefore an object of the present invention to provide a new and useful liner for use in a test cylinder of an apparatus for testing samples of oil well drilling mud or additives.

It is another object of this invention to provide a new and useful liner for use in a test cylinder of an apparatus for testing samples of oil well drilling mud or additives which is made of cast virgin Teflon.

Another object of this invention is to provide a new and useful liner for use in a test cylinder of an apparatus for testing samples of oil well drilling mud or additives which is relatively inexpensive to manufacture.

Another object of this invention is to provide a new and useful liner for use in a test cylinder of an apparatus for testing samples of oil well drilling mud or additives having a lid or closure which moves inside the liner to provide a variable volume therein.

Another object of this invention is to provide a new and useful liner for use in a test cylinder of an apparatus for testing samples of oil well drilling mud or additives which is made of cast virgin Teflon.

Another object of this invention is to provide a new and useful liner for use in a test cylinder of an apparatus for testing samples of oil well drilling mud or additives which is used in combination with a puller.

Other objects of the invention will become apparent from time to time throughout the specification and claims as hereinafter related.

The above noted objects and other objects of the invention are accomplished by a cast virgin Teflon liner which is provided for steel test cylinders used in thermal testing of a sample of drilling mud or additives. The liner has a hollow cylindrical body closed at one end and open at the other. A disc-shaped lid fits inside the open end of the liner and has an elastomeric o-ring for making a tight seal between the liner and lid. A threaded hole in the center of the lid may be closed with threaded plug. The apparatus includes a metal tool or puller, for removing the liner from the test cylinder, and also for removing the lid from the liner. The puller is threaded on the tip end and has a T-shaped handle. An internal air passageway in the puller from a first opening in the tip end of the puller to a second opening on one side of the shaft of the puller allows the lid to be removed from the liner without creating a vacuum in the space between the sample and the lid. For removing the liner from the test cylinder, the threaded shaft is screwed into the lid such that the second opening is covered and thereby creates a vacuum between the sample and lid when the liner is pulled out of the test cylinder. The liner and lid are made of cast virgin Teflon to avoid dangerous chemical reactions, e.g., oxidative reactions, with carbon particles in molded or reused Teflon.

DESCRIPTION OF THE PREFERRED EMBODIMENT

Figure 1:
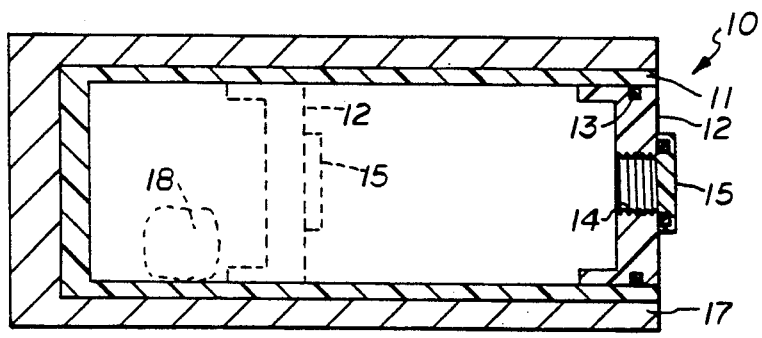
FIG. 1 is a cross-section of the thermal test liner apparatus in accordance with the present invention shown inserted into the test cylinder and having the hole in the center of the lid plugged.
Figure 2:
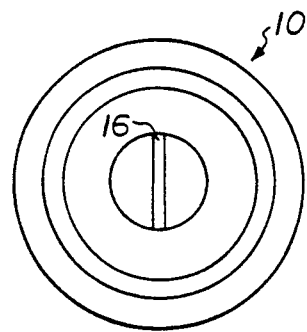
FIG. 2 is a right end elevation of the apparatus of FIG. 1.

Referring to the drawings by numerals of reference, there is shown in FIGS. 1-2, a preferred embodiment of the thermal test liner apparatus 10 in accordance with the present invention. The liner 11 is a cast virgin Teflon member, provided for thermal testing of a sample of drilling mud or additives. Teflon is used for its thermal and lubricating properties and impermeability to gas. Virgin cast Teflon is preferred to avoid dangerous chemical reactions, e.g., oxidative reactions, with carbon particles in molded or reused Teflon.

The liner 11 is a hollow cylindrical body closed at one end and open at the other. A disc-shaped lid 12, of cast virgin Teflon, fits inside the open end of the liner 11 and has an elastomeric O-ring 13 making a tight seal between the liner 11 and lid 12. A threaded hole 14 is located in the center of the lid 11 and may be closed with a cast virgin Teflon threaded plug 15 which has a slot 16 for a screwdriver. Lid 12 is reciprocally movable inside liner 11 (see dotted position in FIG. 1) to vary the volume required for the sample being tested.

The closed liner 11 containing the sample is placed in a test cylinder 17 in a testing apparatus which is subjected to temperature and pressure simulating down-hole conditions to test properties of the mud or additives such as viscosity. Test cylinder 17 is shown as open ended for convenience in illustrating the invention, but in commercial practice, cylinder 17 has a threaded cap (not shown) which closes the cylinder after liner 11 is installed Such a test cylinder is standard in the industry. The particular testing apparatus using this liner assembly is not shown but the liner could be used with the apparatus of Schroeder U.S. Pat. No. 4,677,843.

Figure 3:
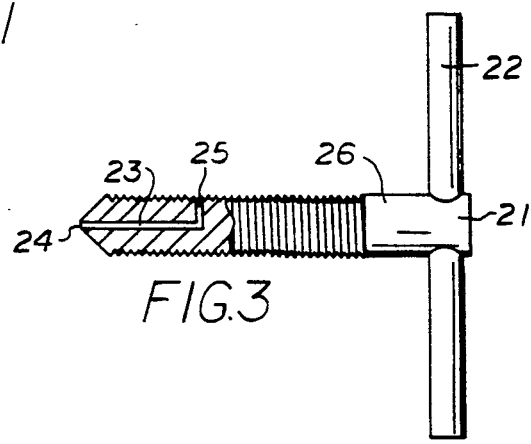
FIG. 3 is a broken cross-section of the puller.
Figure 4:
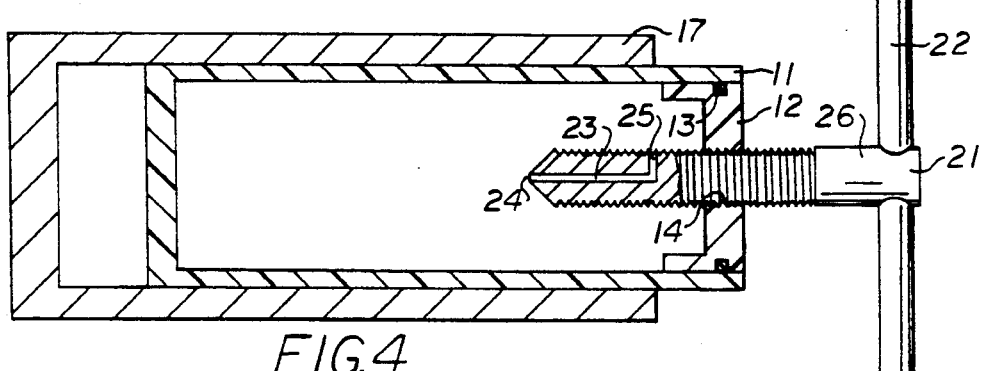
FIG. 4 is a cross-section of the apparatus of FIG. 1 shown with the puller inserted into the hole in the center of the lid.
Figure 5:
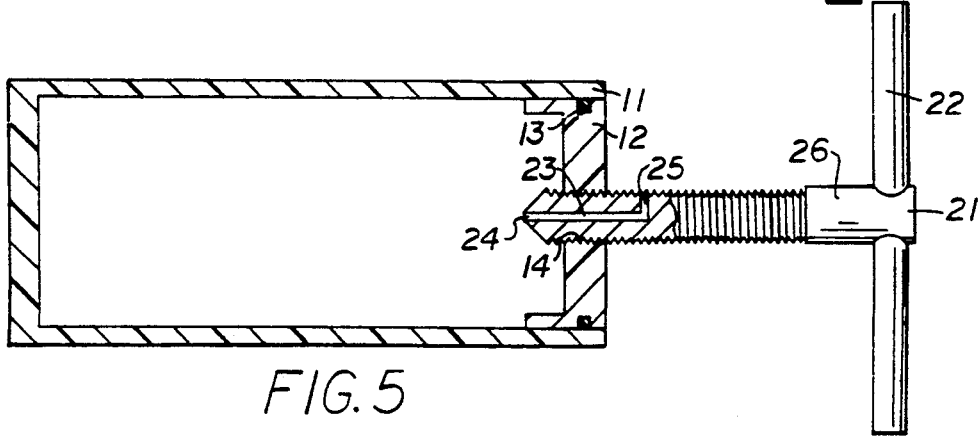
FIG. 5 is a cross-section of the thermal test liner apparatus in accordance with the present invention shown removed from the test cylinder and having the puller inserted into the hole in the center of the lid for pulling the lid out of the liner.

As shown in FIGS. 3-5, the apparatus 10 includes a metal tool or puller 21 with threaded shaft 26, for removing the liner 11 from the test cylinder 17, and also for removing the lid 12 from the liner 11. The puller shaft 26 is threaded from the tip end to a T-shaped handle 22. An internal air passageway 23 in puller shaft 26 allows the lid 12 to be removed from the liner 11 without creating a vacuum in the space between the sample and the lid 12.

The air passageway 23 extends from a first opening 24 in the tip end of the puller shaft 26 to a second opening 25 on one side of the shaft 26. For removing the liner 11 from the test cylinder 17, the threaded shaft 26 is screwed into the lid 12 such that the second opening 25 is inside the liner. Movement of the lid 12 from the dotted position of FIG. 1 to the end of the liner creates a vacuum between the closed end where sample 18 is positioned and lid 12 which resists pulling the lid further and allows the liner assembly 11 to be pulled out of the test cylinder 17 (see FIG. 4).

FIG. 5 shows the liner 11 removed from the test cylinder 17. For removing the lid 12 from the liner 11, the threaded shaft 26 is screwed into the lid 12 such that the second opening 25 is outside the lid 12 and thereby relieves any vacuum created between the sample and lid 12 when the lid 12 is pulled from the liner 11.

OPERATION

The operation of the thermal test liner should be obvious from the description of the preferred embodiment but will be stated herein for clarity A sample 18 for testing is placed in the open liner 11. Lid 12 is placed in the open end of the liner 11 and moved inside the liner to provide a confined space for sample 18 (dotted showing in FIG. 1). Plug 15 is then screwed into threaded opening 14 for sealing, the liner 11. The closed liner 11 containing the sample 18 is placed in a test cylinder 17 and closed by a cap, not shown, for use in a testing apparatus, not shown, which is subjected to temperature and pressure simulating down-hole conditions to test properties of the mud or additives such as viscosity. Increase in temperature inside liner Il increases the pressure and causes lid 12 to move outward. A decrease in temperature inside liner 11 decreases the pressure and causes lid 12 to move inward. Likewise, an increase in pressure outside the liner causes lid 12 to move inward. Lid 12 therefore moves as a floating piston in liner 11. When the testing is completed, and the liner 11 has been cooled down to ambient temperature for handling, plug 15 is removed and threaded shaft 26 of puller 21 is screwed into threaded opening 14 such that the second opening 25 is covered and thereby creates a vacuum between the sample 18 and lid 12 preventing the lid from being removed and allowing the liner 11 to be pulled out of the test cylinder 17. The threaded shaft 26 is then screwed into the lid 12 such that the second opening 25 is outside the lid 12 to relieve any vacuum created between the sample and lid 12 and permit the lid 12 to be pulled from the liner 11.

While this invention has been described fully and completely with special emphasis upon a preferred embodiment, it should be understood that, within the scope of the appended claims, the invention may be practiced otherwise than as specifically described herein.

I claim:

1. A liner for a closed end thermal test cylinder used in a roller oven for testing fluid samples to determine the effects of temperature and various chemical additives on the rheological, filtration, and chemical properties of the sample under simulated circulating conditions, said liner comprising:
   - a cast virgin PTFE hollow cylindrical container, closed at one end and open at the other,
   - a cast virgin PTFE disc-shaped lid having a threaded opening in its center, a peripheral groove and an elastomeric O-ring positioned therein, and
   - said disc-shaped lid being reciprocally movable in said container to enclose a test sample therein and to move in response to changes in pressure of gases from the test sample.

2. A liner according to claim 1 including
   - a cast virgin PTFE threaded plug fitting said threaded opening and an elastomeric O-ring sealing against said disc-shaped lid, and
   - said plug having a slot for a screw driver in a head thereof.

3. A liner according to claim 2 in which:
   - said threaded plug is screwed into the thread opening in the center of said disc-shaped lid, and
   - said disc-shaped lid is placed in the open end of said hollow cylindrical container.

4. A liner according to claim 1 including
   - a pulling tool having a handle and a threaded shaft fitting said threaded opening for removing said liner from said test cylinder, and for removing said lid from said liner.

5. A liner according to claim 4 in which:

said pulling tool is screwed into the threaded opening in the center of said disc-shaped lid, and said disc-shaped lid is placed in the open end of said hollow cylindrical container.

6. A liner according to claim 3 in which:

said pulling tool is screwed into the threaded opening in the center of said disc-shaped lid, said pulling tool shaft has a longitudinal passageway extending from a tip of the shaft and a lateral passageway from an end of said longitudinal passageway, and said disc-shaped lid is placed in the open end of said hollow cylindrical container.

7. In combination, a closed end thermal test cylinder used in a roller oven for testing fluid samples to determine the effects of temperature and various chemical additives on the rheological, filtration, and chemical properties of the sample under simulated circulating conditions, and a liner positioned in said thermal test cylinder comprising a cast virgin PTFE hollow cylindrical container, closed at one end and open at the other, a cast virgin PTFE disc-shaped lid having a threaded opening in its center, a peripheral groove and an elastomeric O-ring positioned therein, and said disc-shaped lid being reciprocally movable in said container to enclose a test sample therein and to move in response to changes in pressure of gases from the test sample.

8. A combination according to claim 7 including a cast virgin PTFE threaded plug fitting said threaded opening and an elastomeric O-ring sealing against said disc-shaped lid, and said plug having a slot for a screw driver in a head thereof.

9. A combination according to claim 8 in which:

said threaded plug is screwed into the threaded opening in the center of said disc-shaped lid, and said disc-shaped lid is placed in the open end of said hollow cylindrical container.

10. A combination according to claim 7 including a pulling tool having a handle and a threaded shaft fitting said threaded opening for removing said liner from said test cylinder, and for removing said lid from said liner.

11. A combination according to claim 10 in which:

said pulling tool is screwed into the threaded opening in the center of said disc-shaped lid, and said disc-shaped lid is placed in the opening end of said hollow cylindrical container.

12. A combination according to claim 10 in which:

said pulling tool is screwed into the threaded opening in the center of said disc-shaped lid, said pulling tool shaft has a longitudinal passageway extending from a tip of the shaft and a lateral passageway from an end of said longitudinal passageway, and said disc-shaped lid is placed in the open end of said hollow cylindrical container.

13. A method for testing fluid samples to determine the effects of temperature and various chemical additives on the rheological, filtration, and chemical properties of the sample under simulated circulating conditions, said method comprising:

providing a roller over for testing fluid samples, providing a closed end thermal test cylinder for use in said oven, providing a liner and positioning the same in said thermal test cylinder, said liner comprising a cast virgin PTFE hollow cylindrical container, closed at one end and open at the other, a cast virgin PTFE disc-shaped lid having a threaded opening in its center, a peripheral groove and an elastomeric O-ring positioned therein, placing a test sample in said liner, placing disc-shaped lid in said liner and moving the same to a position defining a chamber just sufficient to hold said test sample, placing said test cylinder and liner in said oven to heat said test sample, and said disc-shaped lid being reciprocally movable in said container to enclose said test sample therein and to move in response to changes in pressure of gases from the test sample.

14. A method according to claim 13 including providing a cast virgin PTFE threaded plug having an elastomeric O-ring, and a slot for a screwdriver in a head of the plug, and inserting the plug into the threaded opening in the center of said lid after said lid is moved to said position defining a chamber just sufficient to hold said test sample.

15. A method according to claim 14 including providing a pulling tool having a handle and a threaded shaft fitting said threaded opening, removing said plug from said threaded opening after completion of testing, threading said pulling tool into said threaded opening and removing said liner from said test cylinder and removing said lid from said liner therewith.

16. A method according to claim 15 including said pulling tool shaft has a longitudinal passageway extending from a tip of the shaft and a lateral passageway from an end of said longitudinal passageway, and said tool is positioned with said lateral opening inside said lid when pulling said liner from said test cylinder and positioned with said lateral opening outside said lid when pulling said lid from said test cylinder.

* * * * *